(12) United States Patent
Yamamoto et al.

(10) Patent No.: US 9,815,159 B2
(45) Date of Patent: *Nov. 14, 2017

(54) SYSTEM AND METHOD FOR SUBJECTING WEB TO ULTRASONIC PROCESSING

(71) Applicant: UNICHARM CORPORATION, Shikokuchuo-shi, Ehime (JP)

(72) Inventors: Hiroki Yamamoto, Kanonji (JP); Yoshihiko Matsumoto, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 437 days.

This patent is subject to a terminal disclaimer.

(21) Appl. No.: 14/383,069

(22) PCT Filed: Mar. 6, 2013

(86) PCT No.: PCT/JP2013/056121
§ 371 (c)(1),
(2) Date: Sep. 4, 2014

(87) PCT Pub. No.: WO2013/141022
PCT Pub. Date: Sep. 26, 2013

(65) Prior Publication Data
US 2015/0202727 A1 Jul. 23, 2015

(30) Foreign Application Priority Data
Mar. 22, 2012 (JP) .................. 2012-066357

(51) Int. Cl.
*B32B 37/00* (2006.01)
*B23Q 3/18* (2006.01)
(Continued)

(52) U.S. Cl.
CPC .......... *B23Q 3/18* (2013.01); *A61F 13/15593* (2013.01); *B23Q 5/22* (2013.01);
(Continued)

(58) Field of Classification Search
CPC . B23Q 3/186; Y10T 156/1741; Y10T 156/17; B29L 2031/4878; A61F 13/15699
(Continued)

(56) References Cited

U.S. PATENT DOCUMENTS 4,758,293 A * 7/1988 Samida ................... B29C 65/08
156/308.4
5,643,396 A 7/1997 Rajala et al.
(Continued)

FOREIGN PATENT DOCUMENTS

JP 58-039836 A 3/1983
JP 10-513128 A 12/1998
(Continued)

OTHER PUBLICATIONS

International Search Report mailed Apr. 2, 2013 in International Application No. PCT/JP2013/056121, filed Mar. 6, 2013.
(Continued)

*Primary Examiner* — James Sells
(74) *Attorney, Agent, or Firm* — Hauptman Ham, LLP

(57) ABSTRACT

An ultrasonic processing system adapted to subject a web running in a machine direction to ultrasonic processing includes a first mechanical element defined by one of an ultrasonic horn and an anvil and a second mechanical element defined by a remainder. The web placed on an outer peripheral surface of a rotary drum moves conforming to the drum in a machine direction. The first mechanical element is provided on the inner side of the drum and the second mechanical element is provided on the outer side of the drum. The first and second mechanical elements repeat a step of forward movement and a step of backward movement in a direction intersecting the machine direction across the web. In both steps, the first and second mechanical elements come in close contact with each other by the
(Continued)

intermediary of the web and thereby subject the web to the ultrasonic processing.

14 Claims, 11 Drawing Sheets

(51) Int. Cl.
*B29C 65/00* (2006.01)
*B29C 65/08* (2006.01)
*B29C 65/78* (2006.01)
*B23Q 5/22* (2006.01)
*B29L 31/48* (2006.01)
*A61F 13/15* (2006.01)

(52) U.S. Cl.
CPC ........ *B29C 65/087* (2013.01); *B29C 65/7885* (2013.01); *B29C 65/7894* (2013.01); *B29C 66/1122* (2013.01); *B29C 66/21* (2013.01); *B29C 66/232* (2013.01); *B29C 66/431* (2013.01); *B29C 66/7294* (2013.01); *B29C 66/73921* (2013.01); *B29C 66/81433* (2013.01); *B29C 66/8221* (2013.01); *B29C 66/8226* (2013.01); *B29C 66/82261* (2013.01); *B29C 66/836* (2013.01); *B29C 66/8362* (2013.01); *B29C 66/83511* (2013.01); *A61F 13/15739* (2013.01); *A61F 2013/15869* (2013.01); *B29C 66/433* (2013.01); *B29C 66/7352* (2013.01); *B29L 2031/4878* (2013.01)

(58) Field of Classification Search
USPC .................. 156/73.1, 290, 555, 580.1, 580.2
See application file for complete search history.

(56) References Cited

U.S. PATENT DOCUMENTS

| | | | |
|---|---|---|---|
| 5,667,608 A | 9/1997 | Rajala et al. | |
| 6,145,562 A * | 11/2000 | Voss ........................ | B29C 59/04 156/553 |
| 6,537,401 B2 * | 3/2003 | Couillard .............. | B29C 65/087 156/290 |
| 7,383,865 B2 * | 6/2008 | Umebayashi ..... | A61F 13/15739 156/350 |
| 7,887,656 B2 * | 2/2011 | Yamamoto ........ | A61F 13/15699 156/269 |
| 8,211,256 B2 * | 7/2012 | Nakakado ......... | A61F 13/15593 156/163 |
| 8,580,057 B2 * | 11/2013 | Yamamoto ........ | A61F 13/15739 156/290 |
| 2004/0106506 A1 | 6/2004 | Ninomiya et al. | |
| 2010/0116409 A1 | 5/2010 | Yamamoto | |

FOREIGN PATENT DOCUMENTS

| | | |
|---|---|---|
| JP | 2004-330622 A | 11/2004 |
| JP | 2006-192902 A | 7/2006 |
| JP | 2007-030236 A | 2/2007 |
| JP | 2010-115283 A | 5/2010 |
| WO | 2012/042842 A1 | 4/2012 |

OTHER PUBLICATIONS

Extended European Search Report dated Aug. 21, 2015, corresponding to European Patent Application No. 13763570.2.
Written Opinion of the International Searching Authority dated Apr. 2, 2013 in corresponding International Application No. PCT/JP2013/056121 filed Jun. 3, 2013.

* cited by examiner

FIG.2
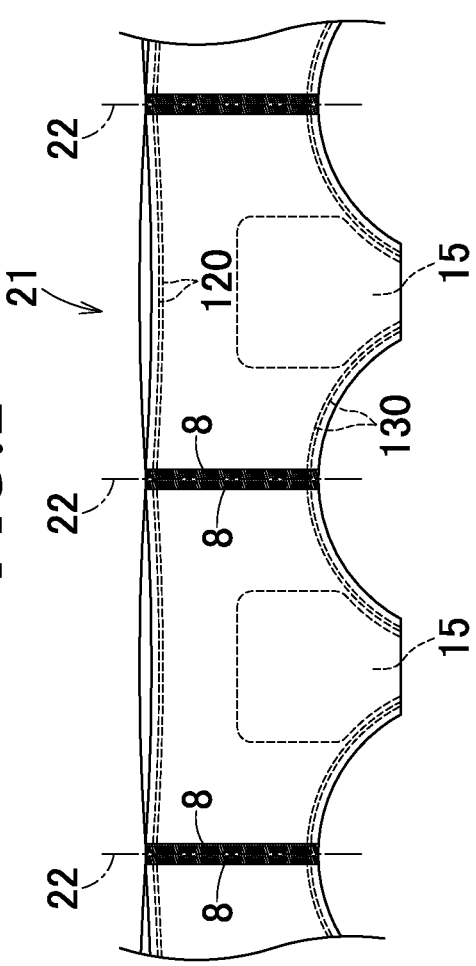
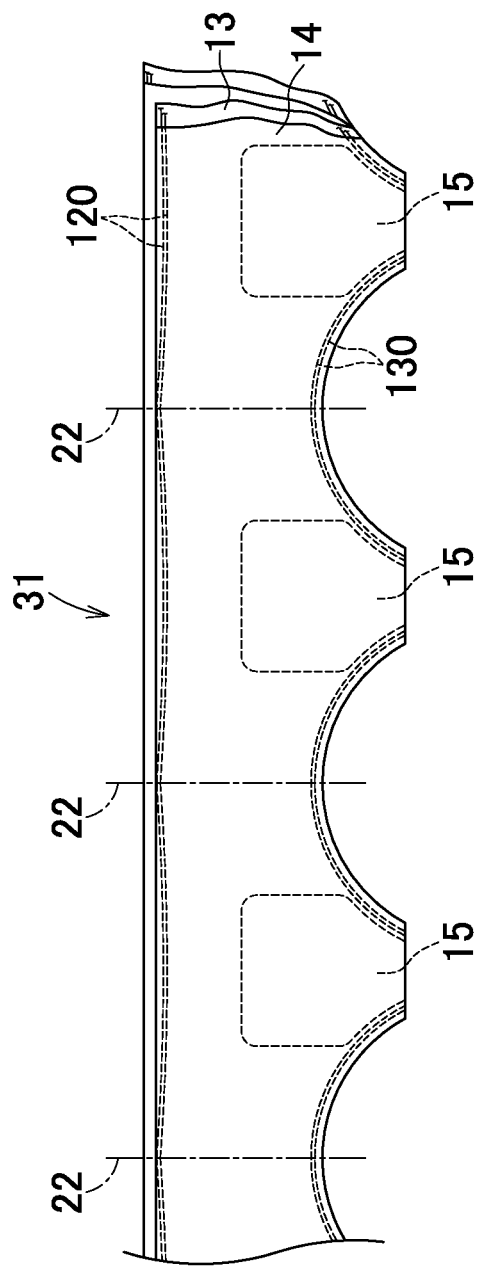

FIG.11
(a)
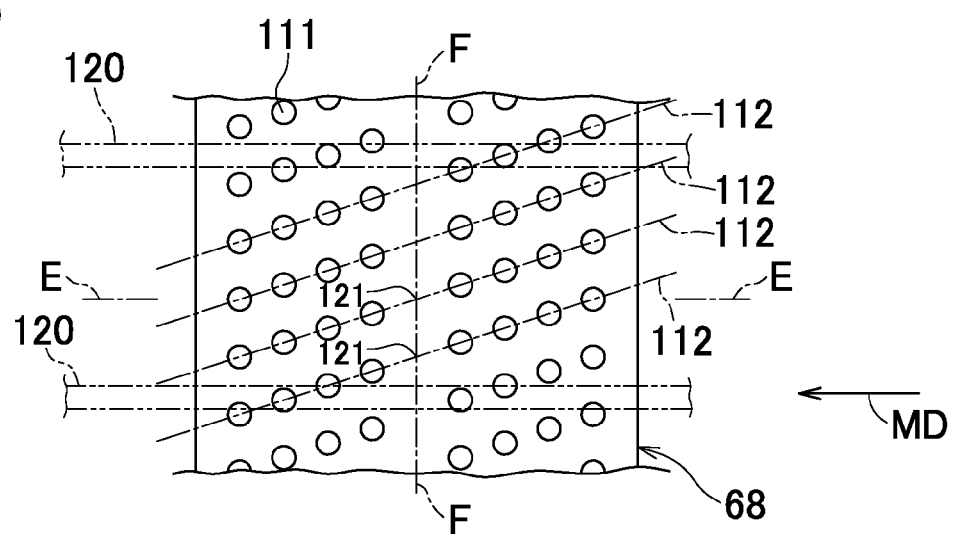
(b)
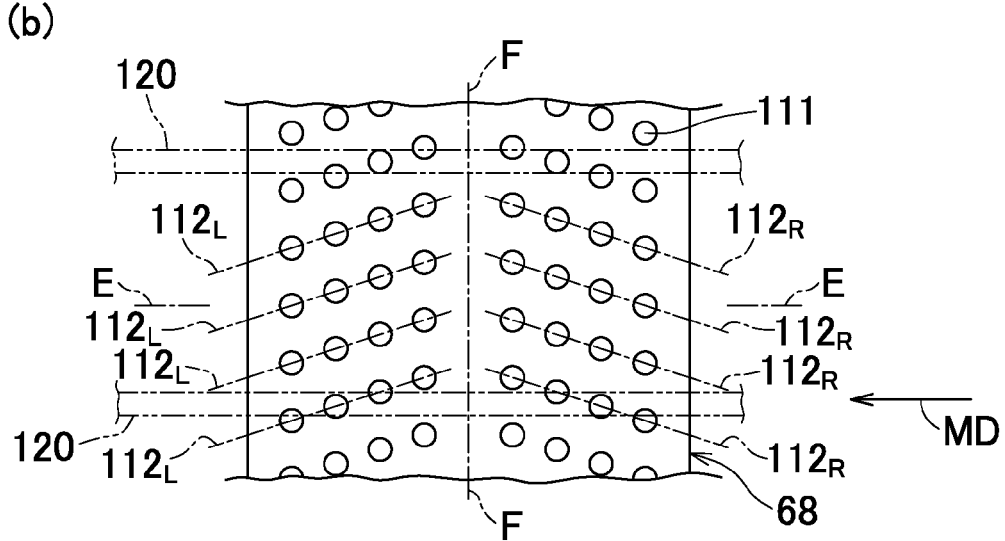

SYSTEM AND METHOD FOR SUBJECTING WEB TO ULTRASONIC PROCESSING

RELATED APPLICATIONS

The present application is a National Phase of International Application Number PCT/JP2013/056121, filed Mar. 6, 2013, which claims priority to Japanese Application Number 2012-066357, filed Mar. 22, 2012.

TECHNICAL FIELD

The present invention relates to systems and methods for subjecting a web continuously running in a machine direction to ultrasonic processing.

BACKGROUND

Apparatuses are known which are adapted to feed a nonwoven fabric containing a thermoplastic synthetic resin or a film formed of a thermoplastic synthetic resin in the form of a web in a machine direction and to subject the web to ultrasonic processing in the course of running.

For example, an ultrasonic apparatus disclosed in the Patent Literature 1 includes an ultrasonic horn applied with ultrasonic oscillation and a hold-down roller cooperating with the ultrasonic horn. The ultrasonic horn rotates around its rotation axis perpendicular to a sheet-like material to be processed and the hold-down roller rotates around its rotation axis extending in parallel to the sheet-like material to be processed so that the material may be subjected to the ultrasonic processing and continuously welded.

A rotary seal system disclosed in the Patent Literature 2 includes a drum rotating in a direction in which the material to be processed in the form of a web runs, a first thermal energy application device attached to a peripheral surface of the drum so as to extend in a direction crossing with the rotational direction of the drum and a second thermal energy application device movably attached to the drum so as to move in a direction crossing with the rotational direction while the second thermal energy application device rotates together with the drum. The material to be processed is disposed between the first thermal energy application device and the second thermal energy application device. During rotation of the drum, the second thermal energy application device cooperates with the first thermal energy application device while the second thermal energy application device moves in the cross direction to apply the material to be processed with thermal energy and, upon completion of the thermal energy application, the second thermal energy application device moves away from the first thermal energy application device to its initial position. One of the first and second thermal energy application devices is a horn applied with ultrasonic oscillation and the other is an anvil.

CITATION LIST

Patent Literature

{PTL 1}: JP S58-39836 A
{PTL 2}: JP H10-513128 A

SUMMARY

Technical Problem

In the apparatus disclosed in PTL 1, each ultrasonic processed portions formed on the web extends in parallel to the machine direction and whereby sealing portions extending in the direction crossing with the machine direction cannot be formed.

In the rotary seal system disclosed in PTL 2, it is possible to form the web running in the machine direction with ultrasonic processed portions in the form of sealing portions extending in the direction crossing with the machine direction. However, in this rotary seal system, the first thermal energy application device is secured to the drum. In addition, the material to be processed is in a stationary state relative to the first thermal energy application device, in other words, in a stationary state relative to the rotary drum when it is applied with the first thermal energy. For the first thermal energy application device used in this manner, there is a likelihood that, during its repeated use, small agglomerations of the thermoplastic synthetic resin constituting the processed material molten under the effect of ultrasonic oscillation might cling to the first thermal energy application device and such small agglomerations eventually might grow to large agglomerations. If such small or large agglomerations move into a gap between the first and second energy application devices, such agglomerations will hinder these two energy application devices from applying the material to be processed with the thermal energy consistently from beginning to end and whereby obtaining sealing portions of desired finishing might be difficult and/or eventually the wearer's skin might be uncomfortably irritated.

An object of the present invention is to provide a system and a method for subjecting a web to ultrasonic processing, which are adapted to overcome the aforementioned problems.

Solution to Problem

The present invention includes a first aspect relating to a system and a second aspect relating to a method.

The first aspect of the present invention relates to an ultrasonic processing system, including first and second mechanical elements configured to subject a web continuously running in a machine direction to ultrasonic processing, the first and second mechanical elements facing each other across the web in a thickness direction of the web.

In this ultrasonic processing system, the first aspect of the present invention further includes the following features:

the system includes an upstream side conveying means and a downstream side conveying means for continuously feeding the web in the machine direction;

a drum having an outer peripheral surface adapted to rotate continuously at the same circumferential velocity as a running velocity of the web and adapted to support the web on the outer peripheral surface is disposed between the upstream side conveying means and the downstream side conveying means;

the outer peripheral surface is provided with an ultrasonic processing portion communicating with an inner side as well as an outer side of the drum;

a first mechanical element configured to be repetitively moved forward and backward in a direction intersecting with the machine direction across the web is disposed on the inner side of the ultrasonic processing portion of the drum;

a second mechanical element configured to be repetitively moved forward and backward together with the first mechanical element is disposed on the outer side of the ultrasonic processing portion of the drum; and the first mechanical element and the second mechanical element cooperate with each other to subject the web positioned in the ultrasonic processing portion to ultrasonic processing in the both steps of moving forward and moving backward but respective home positions of the first and second mechanical elements are drawn apart from each other after completion of the ultrasonic processing in the two steps.

According to one embodiment of the first aspect, the first mechanical element is an ultrasonic horn and the second mechanical element is an anvil.

According to another embodiment of the first aspect, the first mechanical element is the anvil and the second mechanical element is the ultrasonic horn.

According to even another embodiment of the first aspect, the anvil is a roll adapted to rotate both in directions of the forward movement and the backward movement.

According to still another embodiment of the first aspect, biasing means always acting to bias the first mechanical element and the second mechanical element to come close to each other is disposed between the first mechanical element and the second mechanical element.

According to yet another embodiment of the first aspect, cam means are formed on the outer peripheral surface so as to face the respective home positions to which the first mechanical element and the second mechanical element return after the step of forward movement and the step of backward movement, respectively, and the second mechanical element is formed with cam follower means associated with the cam means so that these two means cooperate with each other to draw apart the second mechanical element from the first mechanical element against the biasing effect of the biasing means.

According to further another embodiment of the first aspect, the anvil includes a roll adapted to rotate both in the directions of the forward movement and of the backward movement; the roll has a peripheral surface facing the horn; the peripheral surface is formed with a plurality of bosses arranged with certain intervals both in a circumferential direction and in an axial direction so as to form a plurality of rows extending in parallel to each other and diagonally intersecting with the axial direction, wherein each pair of the adjacent bosses in each of the rows is in such a relationship that, assuming that one boss of adjacent bosses in each of the rows is moved in parallel to the axial direction, the one boss overlaps with a remaining boss, and each pair of the adjacent rows is in such a relationship that, assuming that one boss disposed at one end portion of one of the adjacent rows is moved in parallel to the axial direction, the one boss at least partially overlaps with at least one boss in a remaining row.

The second aspect of the present invention relates to a method for subjecting a web continuously running in the machine direction to repetitive ultrasonic processing by a first mechanical element and a second mechanical element facing each other across the web in its thickness direction of the web.

In this method, the second aspect further includes the following features:

the web is continuously conveyed in the machine direction and placed on an outer peripheral surface of a drum adapted to be continuously rotated in the machine direction at a same circumferential velocity as a running velocity of the web;

the first mechanical element provided on the inside of the drum in an ultrasonic processing portion formed in the outer peripheral surface so as to communicate with both the inside and the outside of the drum and repeating forward movement and backward movement in a direction intersecting the machine direction across the web and the second mechanical element provided on the outside of the drum in the ultrasonic processing portion and repeating forward movement and backward movement together with the first mechanical element are used; and the first mechanical element and the second mechanical element cooperate with each other in steps of forward movement and backward movement to subject the web positioned at the ultrasonic processing portion to ultrasonic processing but respective home positions of the first and second mechanical elements are drawn apart from each other after completion of the ultrasonic processing in the two steps.

According to one embodiment of the second aspect, the first mechanical element is an ultrasonic horn and the second mechanical element is an anvil.

According to another embodiment of the second aspect, the first mechanical element is the anvil and the second mechanical element is the ultrasonic horn.

According to even another embodiment of the second aspect, as the anvil, a roll adapted to rotate both in directions of the forward movement and of the backward movement is used.

According to still another embodiment of the second aspect, biasing means always acting to bias the first mechanical element and the second mechanical element to come close to each other is disposed between the first mechanical element and the second mechanical element.

According to yet another embodiment of the second aspect, cam means are formed on the outer peripheral surface so as to face the respective home positions to which the first mechanical element and the second mechanical element return after the step of forward movement and the step of backward movement, respectively, and the second mechanical element is formed with cam follower means associated with the cam means so that these two means cooperate with each other to draw apart the second mechanical element from the first mechanical element against the biasing effect of the biasing means.

According to further another embodiment of the second aspect, the anvil includes a roll adapted to rotate both in the directions of the forward movement and of the backward movement; the roll has a peripheral surface facing the horn; the peripheral surface is formed with a plurality of bosses arranged with certain intervals both in a circumferential direction and in an axial direction so as to form a plurality of rows extending in parallel to each other and diagonally intersecting with the axial direction, wherein each pair of the adjacent bosses in each of the rows is in such a relationship that, assuming that one boss of adjacent bosses in each of the rows is moved in parallel to the axial direction, the one boss overlaps with a remaining boss, and each pair of the adjacent rows is in such a relationship that, assuming that one boss disposed at one end portion of one of the adjacent rows is moved in parallel to the axial direction, the one boss at least partially overlaps with at least one boss in a remaining row.

Advantageous Effects of Invention

In the system and the method for ultrasonic processing according to the present invention, the first mechanical element defined by one of the ultrasonic horn and the anvil and the second mechanical element defined by a remainder repeat the forward movement and the backward movement in the direction intersecting the machine direction across the web so that the web may be ultrasonically processed in the course of these forward and backward movements and whereby the web may be easily and reliably formed with seams extending in the direction intersecting the machine direction. In addition, even if small agglomerates of a thermoplastic synthetic resin developed during the ultrasonic processing cling to the horn and/or the anvil, these small agglomerates can be removed by the horn and/or anvil moving so as to rub the web. In this way, these small agglomerates should not interfere with the ultrasonic processing.

BRIEF DESCRIPTION OF DRAWINGS

FIG. 2 (a) is a diagram illustrating a series of disposable diapers before cutting into the individual diaper illustrated in FIG. 1, and FIG. 2 (b) is a diagram illustrating a web used to make the series of diapers.

FIG. 11 (a) and FIG. 11 (b) are diagrams exemplifying distribution patterns of bosses.

DESCRIPTION OF EMBODIMENTS

Details of a ultrasonic processing system and a method of ultrasonic processing according to the present invention will be described hereunder with reference to the accompanying drawings.

Figure 1:
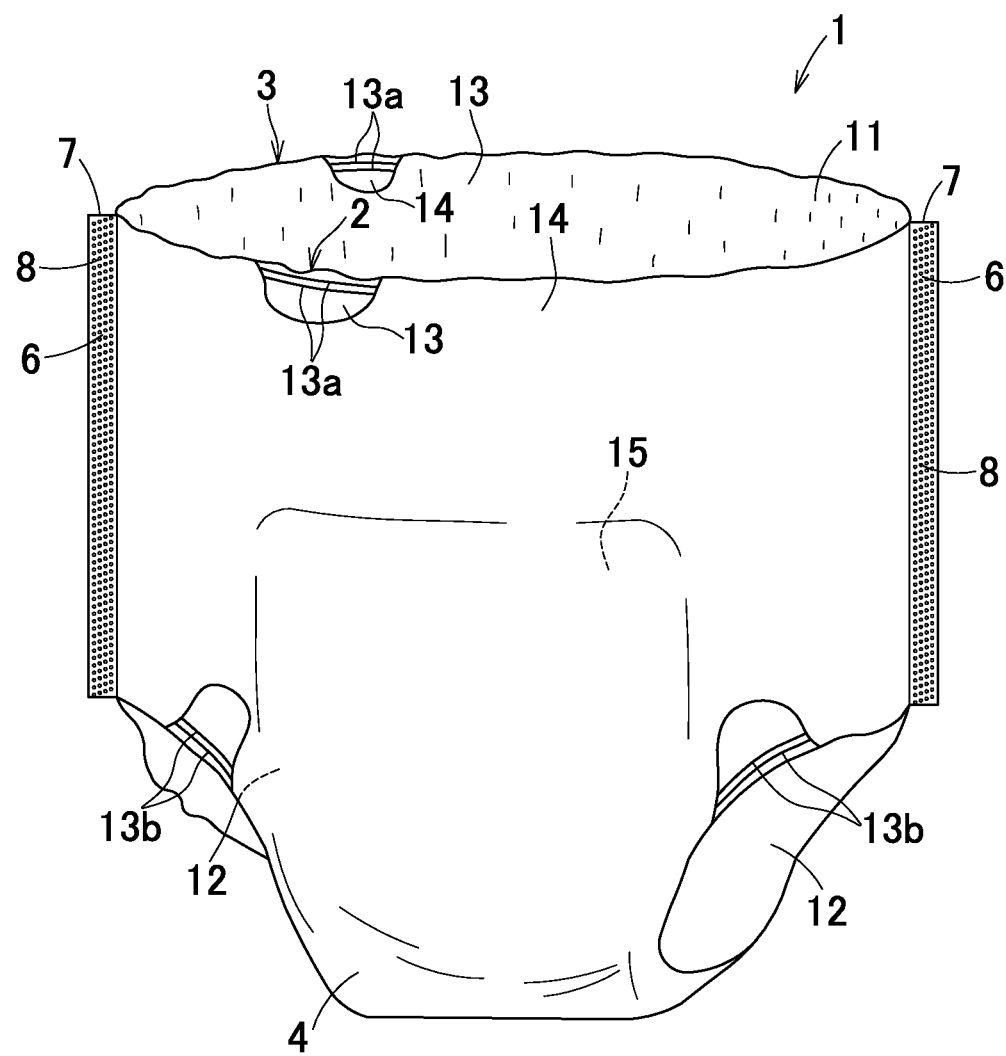
FIG. 1 is a partially cutaway perspective view of a disposable diaper.

FIG. 1 is a partially cutaway perspective view of a disposable pants-type diaper 1 made with the use of an ultrasonic processing system 50 to be hereinafter described. The diaper 1 has a front waist region 2, a rear waist region 3 and a crotch region 4 wherein respective opposite lateral edges 6, 7 of the front waist region 2 and the rear waist region 3 are put flat and joined together at a pair of series of seams 8 and thereupon a waist-opening 11 and a pair of leg-openings 12 are formed. Along peripheries of the waist-opening 11 and the leg-openings 12 elastics 13a, 13b are secured thereto in a stretched or unstretched state. In the front waist region 2, the rear waist region 3 and the crotch region 4, an inner sheet 13 adapted to be put in contact with a wearer's skin is formed of a liquid-permeable nonwoven fabric of thermoplastic synthetic fibers and an outer sheet 14 adapted to be put in contact with the wearer's garment and formed of a laminated sheet composed of a liquid-impermeable film of a thermoplastic synthetic resin and a nonwoven fabric of thermoplastic synthetic fibers and joined to an outer surface of the film. The diaper 1 includes an absorbent structure 15 between the inner and outer sheets 13, 14.

The seams 8 in such a diaper 1 are formed by overlapping the opposite lateral edges 6 of the front waist region 2 and the opposite lateral edges 7 of the rear waist region 3 together and processing them with the ultrasonic processing system 50 to be described later in more details, in other words, by overlapping the inner and outer sheets 13, 14 defining the front waist region 2 and the inner sheet 13 and the outer sheet 14 defining the rear waist region 3 together and processing them with the use of the ultrasonic processing system 50.

FIG. 2 (a) is a partial perspective view illustrating a series of diapers 21 including a plurality of the diapers 1 each illustrated in FIG. 1 contiguously arranged in a width direction and FIG. 2 (b) is a partial perspective view illustrating a web 31 used to make the series of diapers 21 of the diapers 1.

In the series of diapers 21, a plurality of predetermined cutting lines 22 extending in the longitudinal direction are arranged at regular intervals in the transverse direction. On both sides of the respective cutting lines 22, the seams 8 illustrated in FIG. 1 are formed to be adjacent to each other. The diaper 1 illustrated in FIG. 1 can be obtained by cutting such series of diapers 21 along the predetermined cutting lines 22. In FIG. 2 (b), the series of diapers 21 is still in a state of the web 31 having none of the seams 8 and only the predetermined cutting lines 22 are illustrated. Such web 31 may be subjected to ultrasonic processing with the ultrasonic processing system 50 to form the seams 8, thereby obtaining the series of diapers 21 as illustrated in FIG. 2 (a).

Figure 3:
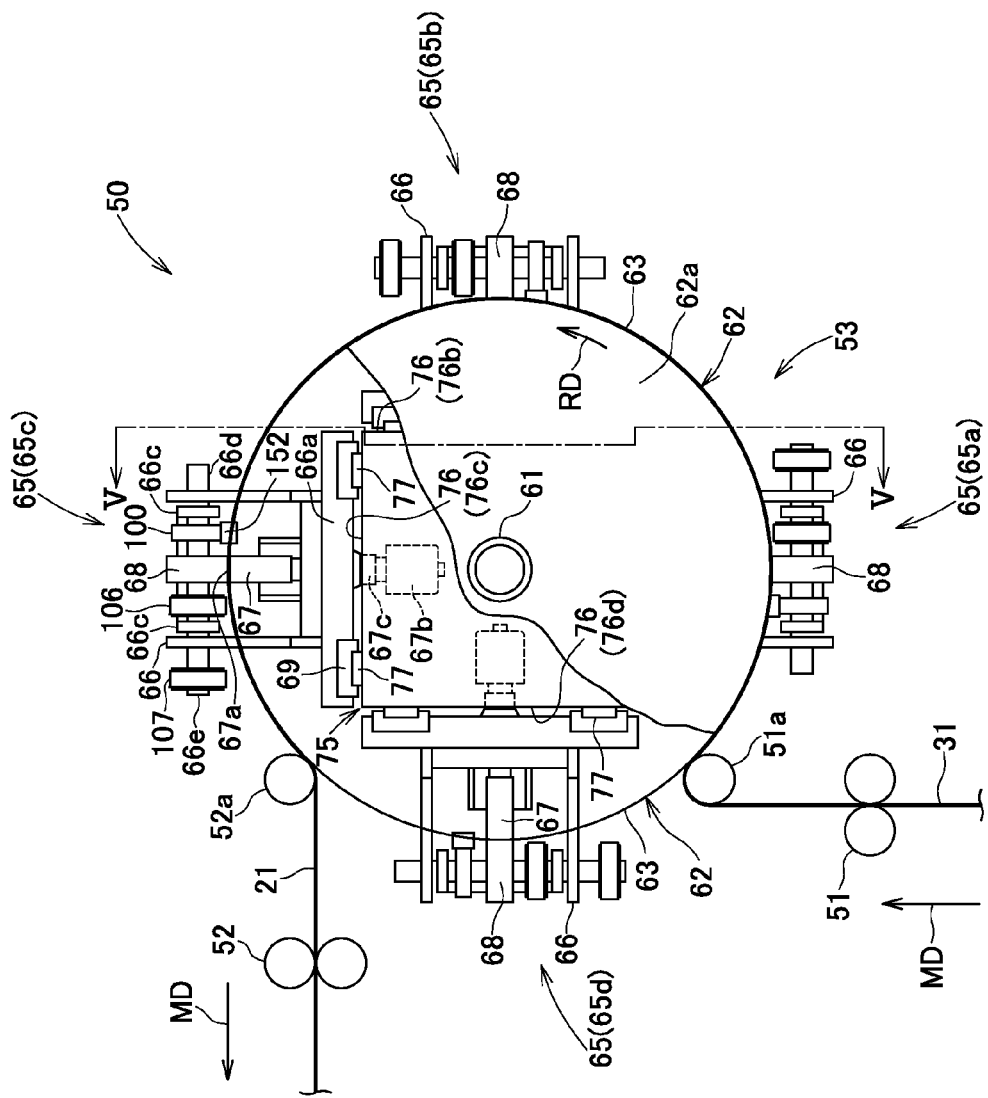
FIG. 3 is a partially cutaway elevation view of an ultrasonic processing system as viewed from an end side of a rotary shaft.

FIG. 3 is a partially cutaway elevation view of the ultrasonic processing system 50 as viewed from an end side of a rotary shaft 61, applying ultrasonic processing to the web 31 illustrated in FIG. 2 (b), thereby obtaining the series of diapers 21 illustrated in FIG. 2 (a), wherein MD indicates a machine direction in which the web 31 runs and RD indicates a rotational direction of a rotary drum 62. The ultrasonic processing system 50 includes a pair of first conveying rolls 51 disposed upstream in the machine direction MD as a conveying means, a pair of second conveying rollers 52 disposed downstream in the machine direction MD also as a conveying means and an ultrasonic processing machine 53 disposed between the first and second conveying rollers 51, 52. The web 31 continuously runs from the first conveying roll 51 to the second conveying roll 52 in the machine direction MD and, in the course of running, passes through a ultrasonic processing apparatus 53. The rotary drum 62 is disposed with a face plate 62a illustrated as being partially broken away which is unrotatable relative to the rotary shaft 61.

The processing apparatus 53 includes the drum 62 rotating together with the rotary shaft 61 in the direction RD and the four ultrasonic processing units (ultrasonic processing units) 65 separately prepared and arranged at regular intervals circumferentially of the drum 62 and adapted to rotate in the direction RD together with the rotary shaft 61. In FIG. 3, these four ultrasonic processing units 65 are designated by reference numerals 65a, 65b, 65c and 65d. The web 31 having passed the first conveying roll 51 is guided by a guide roller 51a to come in close contact with an outer peripheral surface 63 of the drum 62. In the ultrasonic processing machine 53, a running velocity of the web 31 in the machine direction MD and a peripheral velocity of the outer peripheral surface 63 of the drum 62 are preset to be coincident with each other and the outer peripheral surface 63 is previously surface finished or coating finished to prevent from slipping thereon the web 31. Four ultrasonic processing units 65a-65d generically designated by ultrasonic processing units 65 have uniform constructions including, in addition to carriers 66, ultrasonic horns 67 as first mechanical elements in the present invention and anvils 68 as second mechanicals illustrated in FIG. 3.

Figure 4:
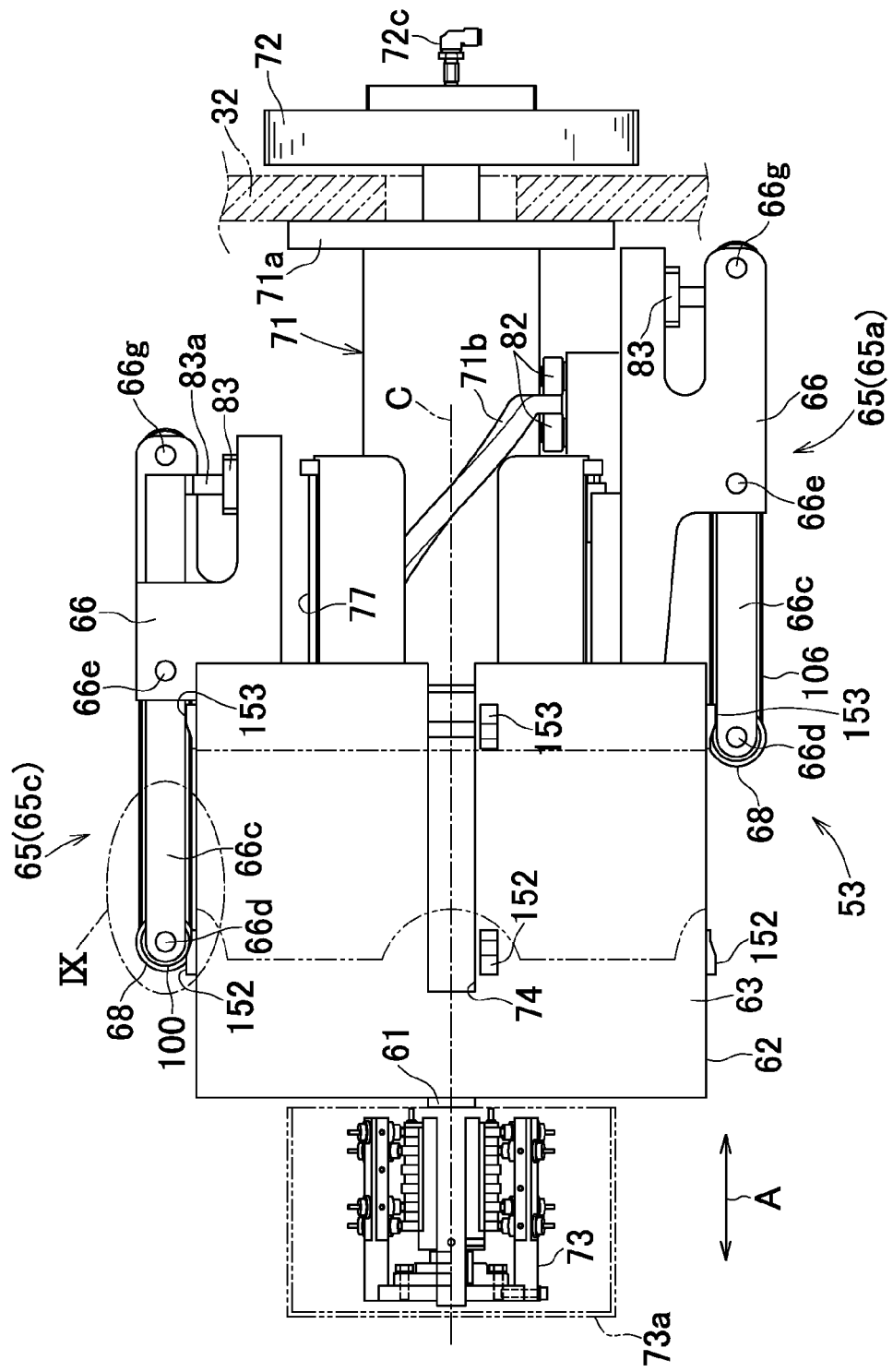
FIG. 4 is a partially omitted side view of the ultrasonic processing system of FIG. 3.

FIG. 4 is a right side elevational view of the ultrasonic processing apparatus 53 of FIG. 3, wherein the web 31 is indicated by an imaginary line and the ultrasonic processing unit 65b is not shown. In FIG. 4, the ultrasonic processing apparatus 53 includes a stationary cylinder 71 secured by the intermediary of a flange 71a to a wall 32 illustrated by an imaginary line on the right hand of FIG. 4 and the rotary shaft 61. The rotary shaft 61 horizontally extends through the stationary cylinder 71 and provided on its right end with an input pulley 72 and on its left end with an ultrasonic electric signal feeding slip ring 73 housed within a protecting casing 73a indicated by an imaginary line. In this regard, both the slip ring 73 and the casing 73a are not shown in FIG. 3. The stationary cylinder 71 is formed on its peripheral surface with a rib-like first cam 71b protruding from the peripheral surface. The rotary shaft 61 having a central axis illustrated by an imaginary line C is rotated by an input main belt (not shown) which is put on the main pulley 72. In addition to the drum 62, a column 75 (See FIG. 3) is secured to the rotary shaft 61 inside the drum 62 and this column 75 also rotates together with the rotary shaft 61 in the direction RD. The column 75 is provided with the carrier 66 attached thereto so that the carrier 66 may be moved back-and-forth in a direction A indicated by a double-headed arrow which is parallel to the rotary shaft 61. In the ultrasonic processing apparatus 53, of the back-and-forth movement in the direction A, a movement from the main pulley 72 toward the drum 62 is a forward movement and a movement from the drum 62 toward the main pulley 72 is a backward movement. The main pulley 72 is provided with a rotary connector 72c adapted to feed respective air cylinders 83 disposed on right ends of the respective ultrasonic processing units 65a-65d with compressed air.

The outer circumferential surface 63 of the drum 62 is partially cut away to form an ultrasonic processing portion 74 in communication with the inside and the outside of the drum 62. The processing portion 74 extends in parallel to the rotary shaft 61 and one end thereof is opened toward the outside of the drum 62. Specifically, such processing portion 74 is formed in association with each of the ultrasonic processing units 65a, 65b, 65c and 65d and, in each of the processing portion 74, the horn 67 is opposed to the associated anvil 68. Slidable movement of the carrier 66 on a slide rail 77 in the column 75 causes each of the ultrasonic processing units 65a-65d to advance leftward or to retract rightward in the direction A. In FIG. 4, the ultrasonic processing unit 65a is illustrated to be at its rearmost position and the ultrasonic processing unit 65c is illustrated to be at its foremost position. In FIG. 3, the ultrasonic processing units 65b, 65d are illustrated to be disposed between their rearmost positions and foremost positions. Each of the ultrasonic processing units 65a-65d makes a shuttle between its rearmost position and foremost position for every rotation of the drum 62 in the direction RD. Details of the back-and-forth movement of these ultrasonic processing units 65a-65d will be described below.

Figure 5:
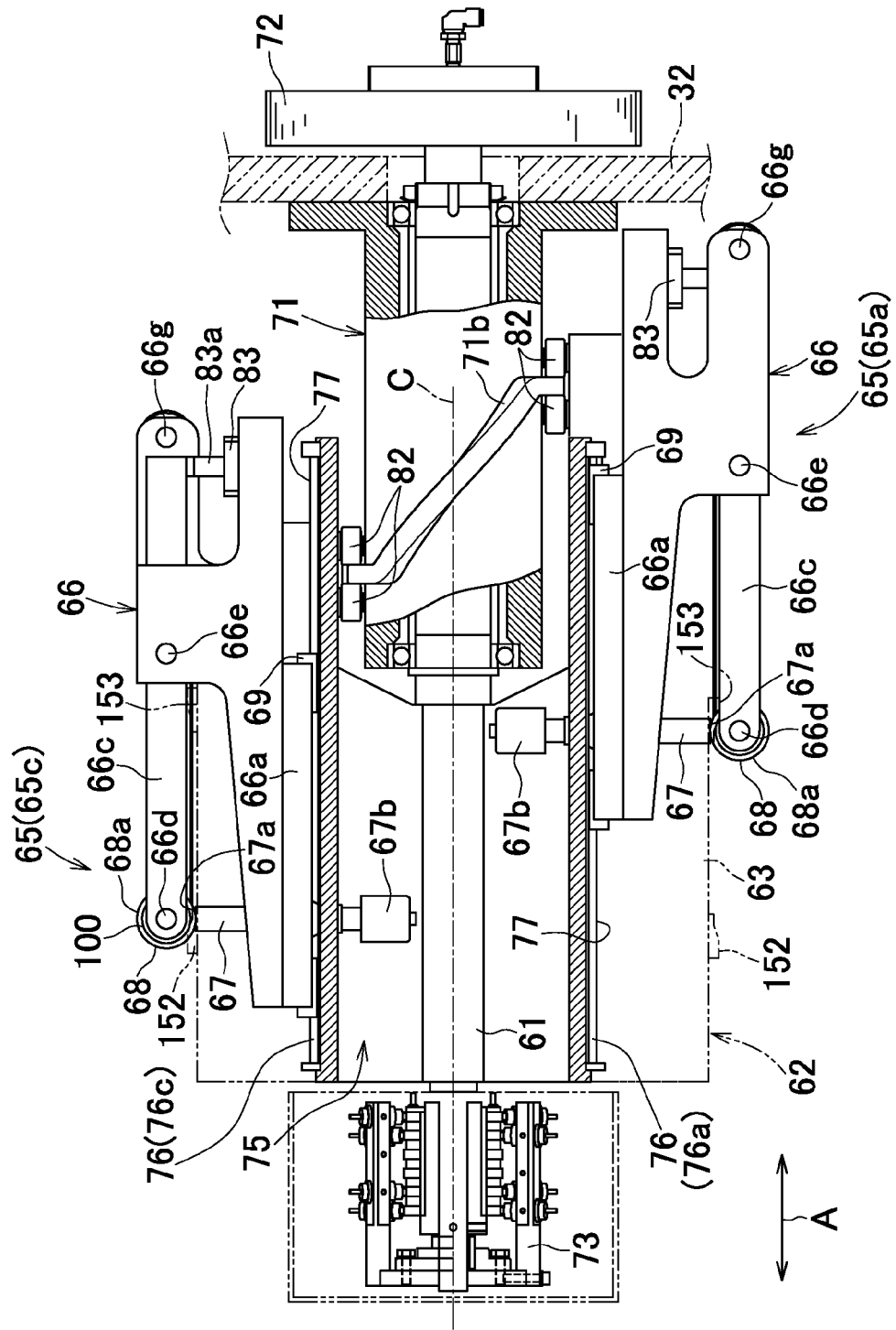
FIG. 5 is a sectional view taken along line V-V in FIG. 3.

FIG. 5 is a partial sectional view taken along line V-V in FIG. 3, wherein the drum 62 has been detached from the rotary shaft 61 and only the outer peripheral surface 63 is illustrated by an imaginary line. For convenience of illustration, hatching is omitted in the cutaway portion. The column 75 provided within the drum 62 has a substantially quadrate cross-sectional shape taken in a direction orthogonal to the rotary shaft 61 so that a surrounding surface 76 of the column 75 includes peripheral surfaces 76a, 76b, 76c, 76d corresponding to the ultrasonic processing units 65a-65d, respectively (See FIG. 3 also). Each of the peripheral surfaces 76a-76d includes a pair of slide rails 77 extending in parallel to the rotary shaft 61. Each of the ultrasonic processing units 65a-65d includes the carrier 66 and the horn 67 and the anvil 68 both attached to the carrier 66. The carrier 66 has a plate segment 66a provided with a slider 69 adapted to move back-and-forth along the slide rail 77 in the direction A. The horn 67 has a flat working surface 67a facing a peripheral surface 68a of the roll-like anvil 68, a booster 67c (See FIG. 3) contiguous to the working surface 67a and a converter 67b electrically connected to the ultrasonic electric signal feeding slip ring 73 (See FIG. 4) wherein a portion disposed between the working surface 67a and the converter 67b is supported by the carrier 66. The working surface 67a is positioned on the peripheral surface 63 on the assumption that none of the ultrasonic processing portions 74 is present on the peripheral surface 63 of the drum 62 and always ultrasonically oscillates in response to signals applied from the slip ring 73 so long as the ultrasonic processing apparatus is in operation. The anvil 68 is attached to a front shaft 66d and rotates together with the front shaft 66d under the action of an inner drive belt 106 (See FIG. 6). Between the working surface 67a of the horn 67 and the peripheral surface 68a of the anvil 68, the web 31 is running over the portion 74 of the drum 62 so that the ultrasonically oscillating working surface 67a of the horn 67 and the peripheral surface 68a of the anvil 68 interleave the web 31 in the thickness direction and cooperate with each other to subject the web 31 to the ultrasonic processing.

Referring again to FIG. 5, the stationary cylinder 71 extending forward from the wall 32 is formed on its peripheral surface with a rib-like first cam 71b and a first cam follower 82 in the carrier 66 for each of the ultrasonic processing units 65a-65d moves conforming to the first cam 71b and causes each of the carriers 66 to move back-and-forth in the direction A. The column 75 is secured to the rotary shaft 61 extending through the stationary cylinder 71 so that the column 75 may rotate together with the rotary shaft 61. The respective peripheral surfaces 76a-76d are provided with the slide rails 77 and the respective carriers 66 in the ultrasonic processing units 65a-65d are placed on the associated slide rails 77 by the intermediary of the sliders 69. The carriers 66 are respectively attached to the associated slide rails 77 in such a manner that the carriers 66 should not be detached from the associated slide rails 77 during a rotation of the drum 62 and the column 75 in the direction RD (See FIG. 5). The foremost position and the rearmost position of the respective carriers 66 for the back-and-forth movement of these carriers 66 are regulated by the first cam 71b. In association with a full revolution of the column 75, for example, the ultrasonic processing unit 65a also rotates in the direction RD and, in the course of a full revolution thereof, the ultrasonic processing unit 65a successively pursues the positions of the ultrasonic processing units 65b, 65c, 65d before the ultrasonic processing unit 65a returns to the position illustrated in FIG. 3.

Figure 6:
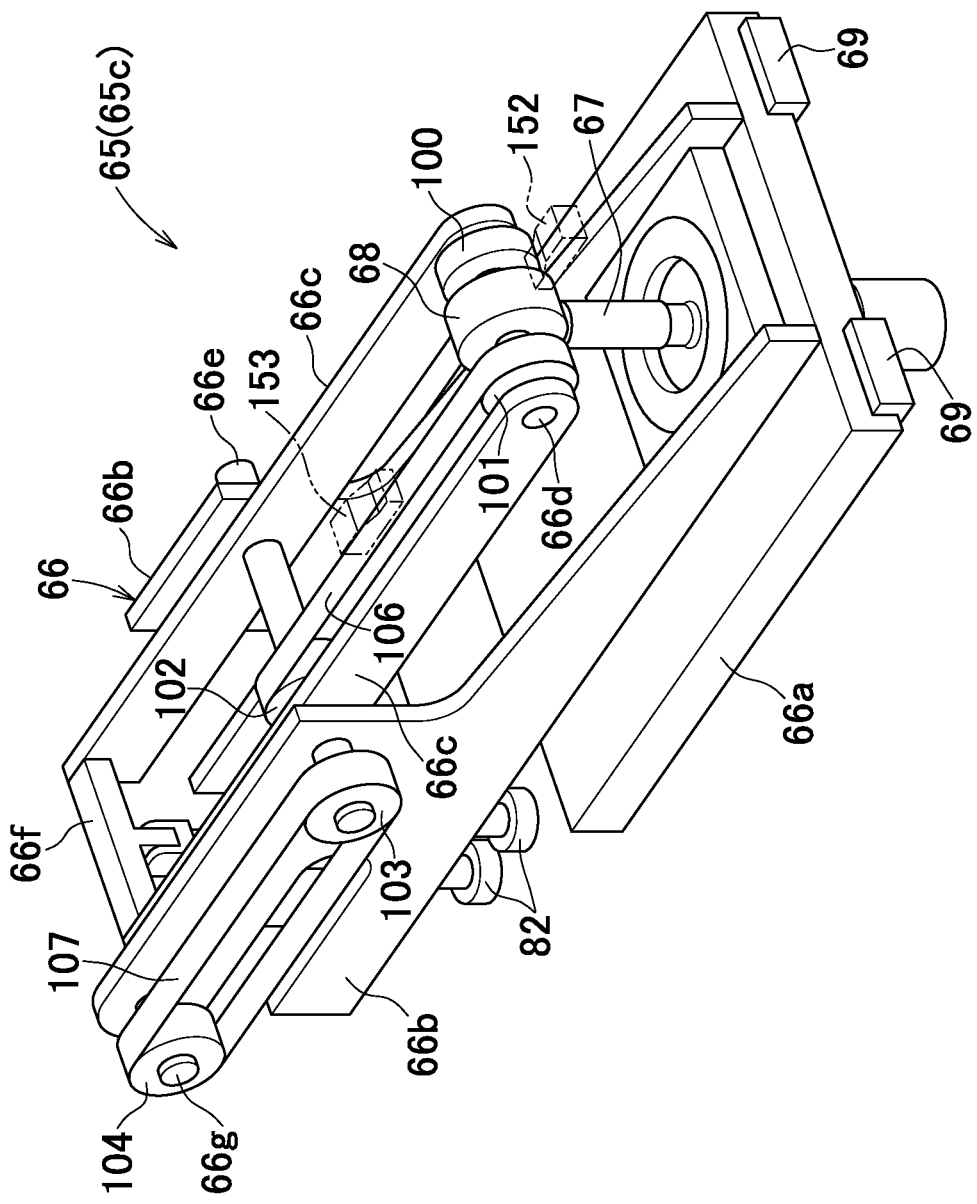
FIG. 6 is a perspective view of an ultrasonic processing unit.
Figure 7:
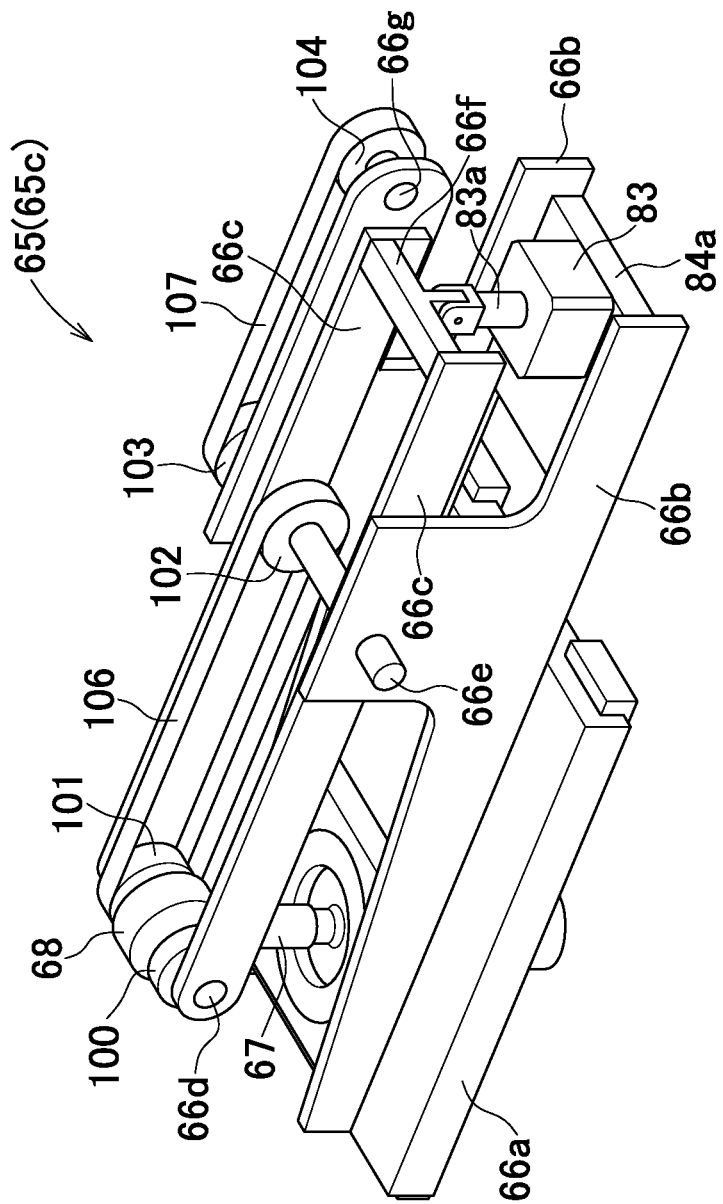
FIG. 7 is a perspective view of the ultrasonic processing unit.

FIGS. 6 and 7 are diagrams illustrating details of the ultrasonic processing units 65 taking the ultrasonic processing unit 65c as an example. FIG. 6 is a perspective view illustrating the ultrasonic processing unit 65c as viewed from the front side and FIG. 7 is a perspective view illustrating the ultrasonic processing unit 65c as viewed from the rear side. The carrier 66 has a pair of supporting walls 66b above the plate segment 66a. Between a pair of supporting walls 66b, the ultrasonic processing unit 65c includes a pair of lateral plates 66c, the rotatable front shaft 66d connecting the paired lateral plates 66c, a rotatable intermediate shaft 66e and a connector plate 66f. To the front shaft 66d, the anvil 68, a roll-like second cam follower 100 and a first small pulley 101 are secured. To the intermediate shaft 66e, a second small pulley 102 is secured. An inner side driving belt 106 is put on the first small pulley 101 and the second small pulley 102. An upper end of a rod 83a of the air cylinder 83 is attached to the connector plate 66f. The intermediate shaft 66e extends outward through one of the paired supporting walls 66b and a third small pulley 103 is secured to this extension portion of the intermediate shaft 66e and, behind the third small pulley 103, a rotatable rear shaft 66g extends outward through one of the paired supporting walls 66b and a fourth small pulley 104 is secured to the rear shaft 66g. An outer position-secured belt 107 is put on the third small pulley 103 and the fourth small pulley 104. In the preferred ultrasonic processing unit 65, as the first-fourth small pulleys 101-104, gear wheels are used and as the inner driving belt 106 and the outer position-secured belt 107, toothed belts are used. Though not shown, the outer position-secured belt 107 is provided on an appropriate region of the column 75 in a stationary state relative to the carrier 66 adapted to move back-and-forth. In the ultrasonic processing unit 65c constructed in this manner, compressed air is fed from the rotary connector 72c in the main pulley 72 and the rod 83a pushed upward the connector plate 66f. Such movement of the rod 83a causes a pair of the lateral plates 66c to rotate about the intermediate shaft 66e and always biases the anvil 68 to come closer to the horn 67.

In the ultrasonic processing unit 65c rotating in the direction RD together with the rotary shaft 61, the first cam follower 82 moves conforming to the configuration of the first cam 71b and whereby the ultrasonic processing unit 65c moves back-and-forth in the direction A. During such back-and-forth movement of the ultrasonic processing unit 65c, the third small pulley 103 and the fourth small pulley 104 are engaged with the outer position-secured belt 107, thereby being rotated. The rotation of the third small pulley 103 causes the second small pulley 102 to be rotated and whereby the inner driving belt 106 is rotated and the first small pulley 101 also is rotated. Rotation of the first small pulley 101 causes the anvil 68 and the second cam follower 100 to be rotated. Both the anvil 68 and the second cam follower 100 are rotated in the direction of forward movement when the ultrasonic processing unit 65c moves forward and the anvil 68 and the second cam follower 100 are rotated in the direction of backward movement when the ultrasonic processing unit 65c moves backward.

Figure 8:
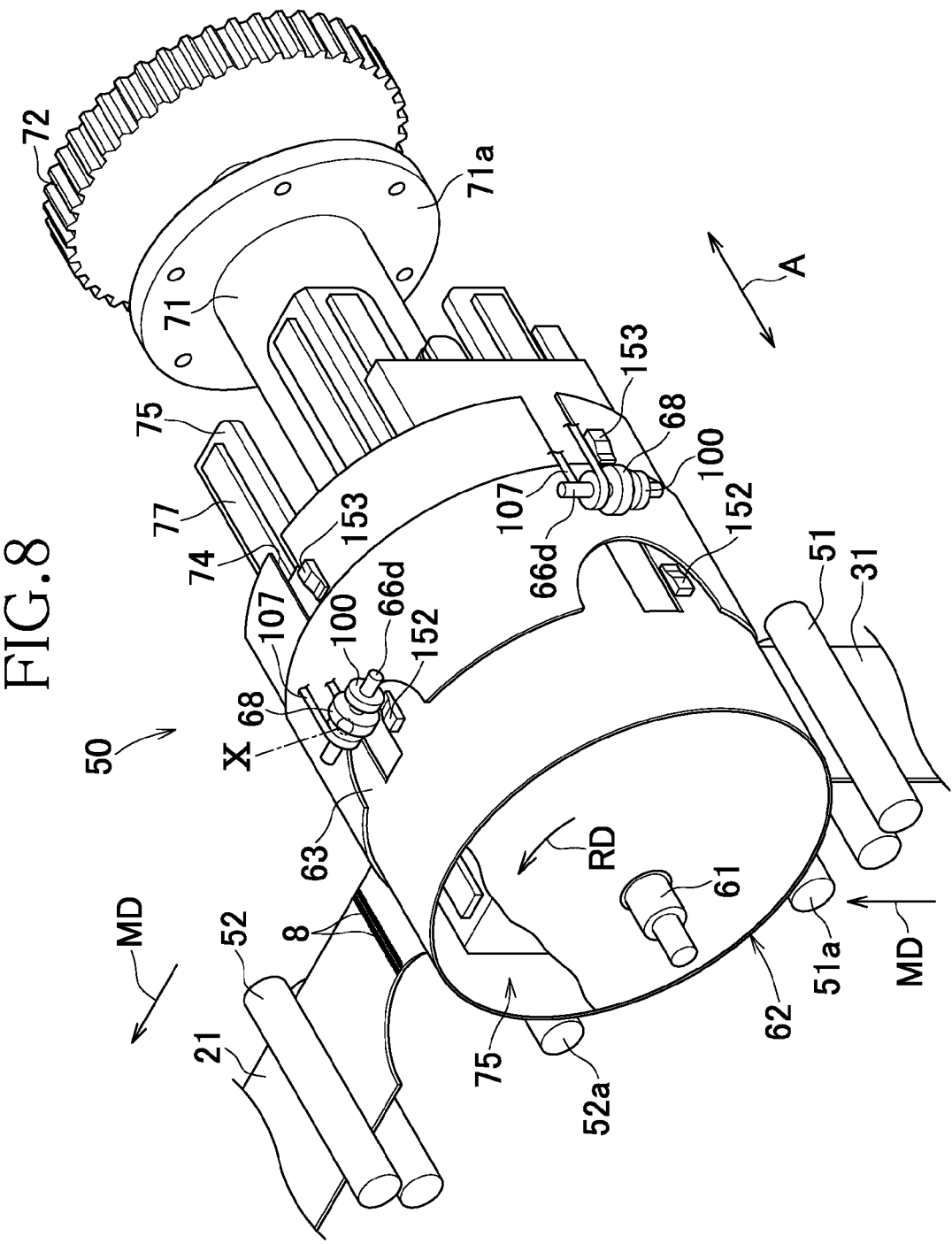
FIG. 8 is a schematic diagram of a ultrasonic processing apparatus to illustrate a flow of web.

FIG. 8 is a schematic diagram illustrating the ultrasonic processing system 50 in which the web 31 placed on the peripheral surface 63 of the drum are being subjected to the ultrasonic processing under a cooperation of the horn 67 and the anvil 68. For convenience of illustration, the members which would otherwise interfere with illustration of the web 31 placed on the drum 62 are not shown in FIG. 8. Ultrasonic processing of the web 31 guided by the guide roll 51a to be placed on the peripheral surface 63 is started when the ultrasonic processing unit 65 disposed on the position of the ultrasonic processing unit 65c in FIG. 3 begins to move forward and ultrasonic processing of the web 31 guided by the guide roll 51a to be placed on the peripheral surface 63 is terminated when the ultrasonic processing unit 65 disposed on the position of the ultrasonic processing unit 65c in FIG. 3 has moved back to the initial position. Now the web 31 converted to the series of diapers 21 as illustrated in FIG. 2 is conveyed out from the ultrasonic processing system 50 by the second conveying roll 52 serving as the conveying means for the series of diapers 21.

In the ultrasonic processing system 50, when the web 31 running together with the drum 62 in the machine direction MD is ultrasonically processed by the horn 67 and the anvil 68, the working surface 67a of the horn 67 slidably moves along the web 31 across the web 31 in the direction A. In consequence, even if the thermoplastic synthetic resin contained in the web 31 is molten as a result of the ultrasonic processing, part of such a molten thermoplastic synthetic resin forms small agglomerates having a length, for example, in a range of 2 to 5 mm and is transferred from the web 31 to the horn 67, such small agglomerates wiped away by the web 31 when the horn 67 moves so as to rub the web 31 without a possibility that the small agglomerates might stay between the horn 67 and the anvil 68 and interfere with the ultrasonic processing. Such small agglomerates should not cling to the individual diaper 1 obtained from a series of diapers 21 and irritate the wearer's skin.

In the ultrasonic processing system 50, the anvil 68 also moves across the web 31 while rotating so as to rub the web 31 and, in consequence, the small agglomerates of the thermoplastic synthetic resin contained in the web 31 should not cling to the anvil 68. To prevent such small agglomerates of a thermoplastic synthetic resin from clinging to the anvil 68, heating means or cooling means may be used. For example, it is possible to use the anvil 68 in a state heated at a temperature in a range of 70 to 80° C. or higher or in a state cooled at a temperature in a range of 0 to −5° C.

Figure 9:
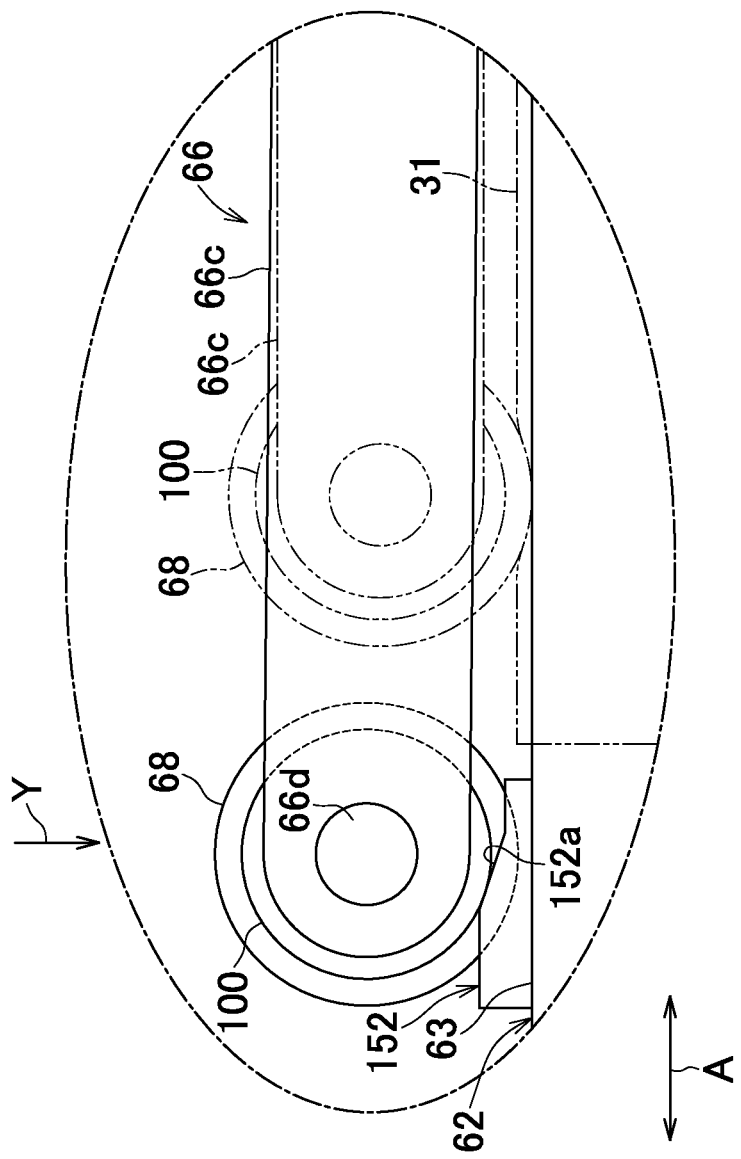
FIG. 9 is a scale-enlarged diagram illustrating portion IX in FIG. 4.

FIG. 9 is a scale-enlarged diagram illustrating portion IX in FIG. 4. In FIG. 4, the peripheral surface 63 of the drum 62 is provided with the second cam 152 and the third cam 153. The second cam 152 defines an end point for the forward movement of the carrier 66 and the third cam 153 defines an end point for the backward movement of the carrier 66. The front shaft 66d (See FIG. 7) of the carrier 66 is provided with the roll-like cam follower 100.

Referring to FIG. 9, a second cam 152 and a third cam 153 are formed so that respective slope faces 152a, 153a thereof may be opposed to each other in the direction A, i.e., in a back-and-forth direction of the ultrasonic processing system 50. The anvil 68 being always biased downward under a pressure of the rod 83a of the cylinder 83 indicated by an arrow Y in FIG. 9 so that the anvil 68 may be put in close contact with the horn 67 by the intermediary of the web 31. Both in the step of the forward movement of the carrier 66 and in the step of the backward movement of the carrier 66, the anvil 68 moves forward and backward together with the horn 67 to subject the web 31 to the ultrasonic processing. In FIG. 9, the anvil 68 working in this manner is indicated by an imaginary line. In this regard, if the anvil 68 continues its forward movement or backward movement beyond the web 31 in these two steps even after the ultrasonic processing of the web 31 has been completed, the second cam follower 100 having a diameter smaller than that of the anvil 68 rolls up the slope face 152a of the second cam 152 or rolls up the slope face 153a of the third cam 153 to move upward the front shaft 66d and the anvil 68 attached to this front shaft 66d as viewed in FIG. 9 against a biasing effect of the cylinder 83 and thereby to separate the anvil 68 off from the horn 67 in a diametric direction of the drum 62. In this way, it is ensured that the anvil 68 is prevented from coming in contact directly as well as indirectly with the horn 67 being ultrasonically oscillating. In the case exemplified in FIG. 9, after the ultrasonic processing in the step in which the anvil 68 indicated by the imaginary line moves leftward has been terminated, the second cam follower 100 rolls up the slope face 152a of the second cam 152 to the position indicated by a solid line.

In the ultrasonic processing system 50 in which the anvil 60 moves in this manner, it is possible to avoid a situation in which the ultrasonically oscillating horn 67 comes in direct contact with the anvil 68 on the outer side of the web 31 in the direction A, namely, on the outer side of the web 31 in its width direction or it is possible to limit such situation to the minimum time period. Therefore, it is possible to prevent the top surface 67 of the horn 67 serving as the working surface and the working surface 68a of the anvil 68 from being damaged due to direct contact with each other. As a result, it is also possible in the ultrasonic processing system 50 to prevent the region of the web 31 to be ultrasonically processed from being soiled with metallic powder due to the contact between the horn 67 and the anvil 68. Further, during operation, the ultrasonic processing system 50 is in a state in which the anvil 68 is indirect or direct contact with the horn 67 or the anvil 68 is in close contact with the second cam 152 or the third cam 153 and therefore the drum 62 can be rotated at a high velocity without noticeably oscillating.

In the ultrasonic processing system 50, positions of both the second cam 152 and the third cam 153 used in this manner on the peripheral surface 63 of the drum 62 may be changed as occasion demands. For example, the second cam 152 and the third cam 153 can be brought closer to the web 31 in the direction A so that the anvil 68 may begin to follow the second cam 152 or the third cam 153 and whereby the horn 67 and the anvil 68 may be prevented from coming in contact with each other immediately after the anvil 68 has moved across the web 31. The first cam 71b preferably has a shape and a dimension which conform with locations of the second cam 152 and/or the third cam 153.

In the ultrasonic processing system 50, it is unnecessary to stop the ultrasonic oscillation of the horn 67 during such forward and backward movement of the anvil 68 and therefore the diaper 1 can be produced at a speed higher than the system in which the ultrasonic oscillation must be turned on and off at short intervals.

In addition, in the step of forward movement and in the step of backward movement, the horn 67 and the anvil 68 cooperate with each other to repeat the ultrasonic processing to the same portion of the web 31 which is in the stationary state. In this way, the joint strength of the seams 8 formed on the web 31 can be reliably improved.

Figure 10:
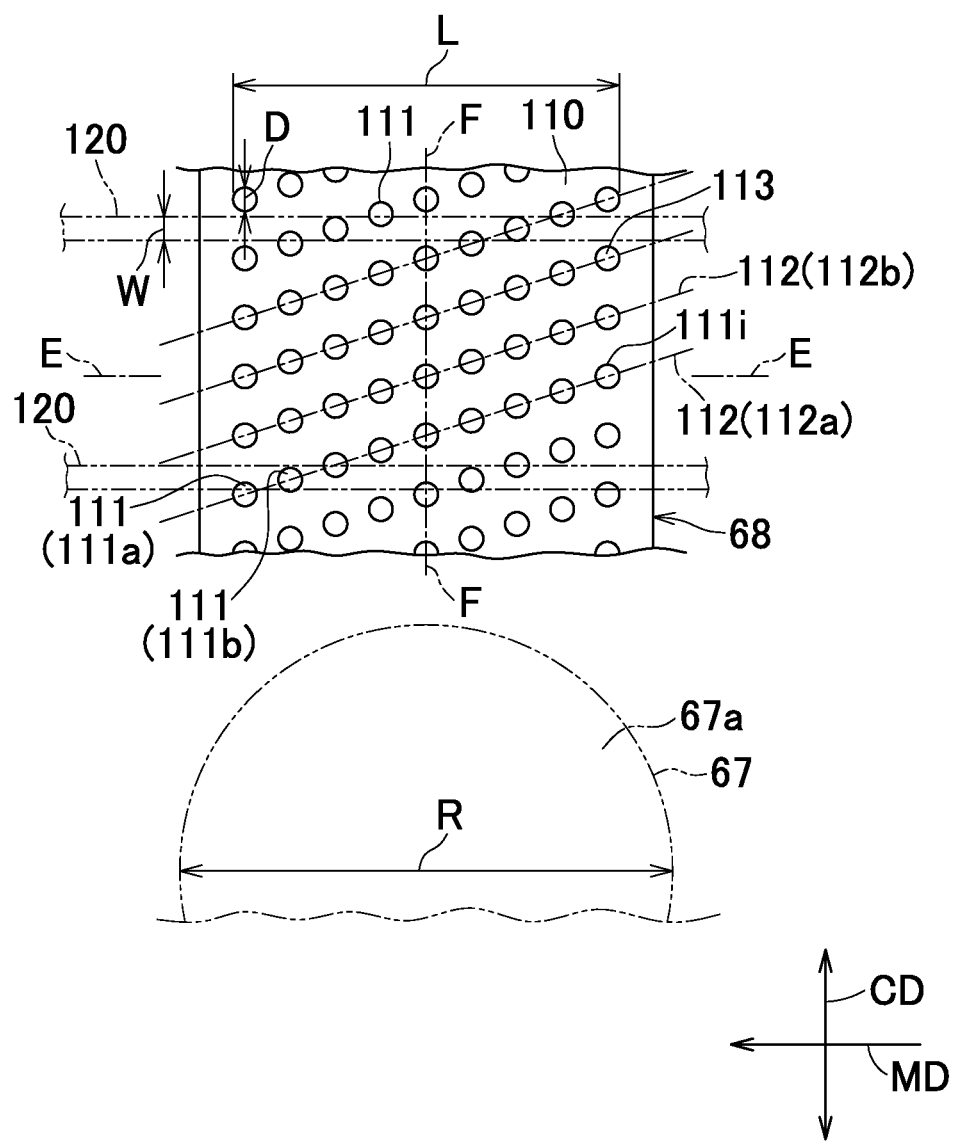
FIG. 10 is a scale-enlarged diagram illustrating portion X in FIG. 8.

FIG. 10 is a scale-enlarged diagram illustrating portion X in FIG. 8. While portion X is an arcuate portion of a peripheral surface 110 of the anvil 68, this portion X is illustrated in FIG. 10 in a flatly developed state. The peripheral surface 110 is formed with a plurality of cylindrical bosses 111 having the same shape arranged in a circumferential direction as well as in an axial direction. In FIG. 10, a part of the working surface 67a of the horn 67 is indicated by an imaginary line to proclaim that the part of the working surface 67a has a dimension R to be described later.

Referring to FIG. 10, each of the bosses 111 has a flat top face 113. A dimension from the peripheral surface 110 to the top face 113, i.e., a height of the protrusion 111 may be appropriately selected depending on the thickness of the web 31. For example, the bosses 111 for manufacturing the disposable diaper 1 preferably each have this dimension in a range of 0.5 to 5 mm. The bosses 111 exemplified define rows arranged at regular or substantially regular intervals so as to intersect obliquely with an axis line E-E of the front shaft 66d and each of the rows has a dimension L in a direction parallel to the axis line E-E. For example, in the row 112a, assuming that one (for example, 111a) of the adjacent bosses 111a and 111b is moved in parallel to the axis line E-E, this protrusion 111a will at least partially overlap the adjacent protrusion (111b). Such relationship is maintained also on the arcuate peripheral surface 110. With use of the anvil 68 having the bosses 111 which form such rows 112 for the ultrasonic processing, it is ensured that the flat top faces 113 of the bosses 111 and the flat working surfaces 67a of the horn 67 are always kept in close contact with each other across the web 31. In this way, it is assured to avoid a problem that the flat working surface 67a of the horn 67 might be repetitively pressed against only the peripheries of the top face 113 of the protrusion 111 and the pressure might be repetitively concentrated on restricted regions, resulting in deteriorating the desired flat and smooth properties of the working surface 67a. In this regard, the dimension R of the working surface 67a of the horn 67 indicated in FIG. 10 is the dimension in the axial direction of the anvil 68 and set to be larger than the dimension L of the row 112 in the anvil 68.

Referring again to FIG. 10, rubber threads 120 attached under tension or under no tension to the web 31 (See FIG. 2) formed, for example, of thermoplastic synthetic fibers are indicated by imaginary lines. The rubber threads 120 are attached by means, for example, of hot melt adhesive (not shown) to the web 31 and rectilinearly extend in the machine direction MD which is parallel to the axis line E-E. These rubber threads have a dimension in a cross direction CD being orthogonal to the machine direction MD. While an upper limit value of the dimension D of the protrusion 111 in the cross direction CD is constrained to a value slightly larger than the dimension W, in each of the more preferred bosses, the dimension D is equal to the dimension W or smaller than the dimension W. The upper limit of the dimension D corresponds to the dimension of the rubber threads 120 in the cross direction CD when the rubber threads have been deformed as a result of close contact between the horn 67 and the anvil 68 across the web 31. Such correlation between the dimension D and the dimension W ensures that the bosses 111 do get across the rubber threads in the cross direction CD even when the rubber threads 120 are compressed between the bosses 111 and the horn 67, in other words, the bosses 111 only partially compress the rubber threads 120. Consequently, a possibility that the rubber threads 120 might be cut in the step of the ultrasonic processing of the web 31 can be avoided or substantially avoided. Furthermore, the rubber threads can be reliably pressure-bonded to the web 31 under the working of the bosses 111. As will be apparent from FIG. 10, the rows 112 of the bosses 111 are arranged so that the rubber threads 120 may be surely pressed by any one or more of the bosses 111 when the rows 112 of the bosses 111 intersect with the rubber threads 120 extending in parallel to axis line E-E. In this regard, the cross direction CD in FIG. 10 corresponds to the direction A in FIG. 8.

FIGS. 11 (a) and (b) exemplarily illustrate a distribution pattern of the bosses 111 on the anvil 68. In FIG. 11(a), the bosses 111 form the rows similar to the bosses 111 in FIG. 10. However, none of the bosses 111 is present on an intersection 121 between a central line F-F bisecting a width of the anvil 68, namely, a dimension of the anvil 68 in parallel to the axial line E-E and the row 112 and in the vicinity of this intersection 121. If the anvil 68 illustrated in FIG. 11 (a) is used to treat the web 31 illustrated in FIG. 2 (b) and center line F-F is aligned with the predetermined cutting line 22 of the web 31, each pair of seams 8 adjacent to each other across the predetermined cutting line 22 can be formed with use of a plurality of bosses 111. The sheet materials 13, 14 illustrated in FIG. 1 which overlap each other are not joined to each other between each pair of the adjacent seams 8and a region defined by the predetermined cutting line will be kept in a flexible and comfortable texture.

In FIG. 11 (b), the bosses 111 are arranged symmetrically about center line F-F. On the left side of center line F-F, the bosses 111 form the rows $112_L$ having gradient from bottom left to top right relative to axial line E-E and on the right side of center line F-F, the bosses 111 form the rows $112_R$ having gradient from bottom right to top left relative to axial line E-E. An arrangement of the bosses 111 in each row and an arrangement of the bosses 111 between each pair of the adjacent rows are similar to those in FIG. 10.

While the bosses 111 on the anvil 68 according to the present invention may be arranged in the pattern as exemplified, the present invention is not limited to the arrangement as exemplified. For example, it is possible to distribute the bosses 111 in an irregular pattern. The shape of the top face 113 of the protrusion 111 is also not limited to the exemplified shape but freely selected.

In the ultrasonic processing system 50 having been exemplified and described, the anvil 68 as the second mechanical element disposed on the outside of the drum 62 is biased to move closer to the web 31. In this regard, when the ultrasonic processing system 50 is caused to stop operation, the cylinder 83 may be actuated to draw apart the anvil 68 from the web 31. While the ultrasonic processing system 50 exemplified and described is used for the purpose of welding the web 31, the ultrasonic processing system may be also used for the purpose of partially cutting the web 31 and welding the web 31 along a periphery of the cut region.

It is also possible to implement the present invention in such a manner that the horn 67 defines the second mechanical element disposed on the outside of the drum 62 and the anvil 68 defines the first mechanical element disposed on the inside of the drum 62.

REFERENCE SIGNS LIST 31 web
50 ultrasonic processing system
51 conveying means (conveying rolls)
52 conveying means (conveying rolls)
61 central axis
62 drum
63 outer peripheral surface
67 first mechanical element (horn)
67a working surface
68 second mechanical element (anvil)
74 processing portions
83, 83a biasing means
100 cam follower means (second cam follower)
110 peripheral surface
111 bosses
112 rows
152 cam means (second cam)
153 cam means (third cam)
C2 axis (center line)
E-E axial direction (axis line)
MD machine direction

The invention claimed is:

1. An ultrasonic processing system, comprising:
first and second mechanical elements configured to subject a web continuously running in a machine direction to ultrasonic processing, wherein the first and second mechanical elements face each other across the web in a thickness direction of the web;
an upstream side conveying means and a downstream side conveying means for continuously feeding the web in the machine direction; and
a drum having an outer peripheral surface adapted to rotate continuously at the same circumferential velocity as a running velocity of the web and adapted to support the web on the outer peripheral surface,
wherein
said drum is disposed between the upstream side conveying means and the downstream side conveying means,
the outer peripheral surface is provided with a ultrasonic processing portion communicating with an inner side as well as an outer side of the drum,
the first mechanical element configured to be repetitively moved forward and backward in a direction intersecting with the machine direction across the web is disposed on the inner side of the ultrasonic processing portion of the drum,
the second mechanical element configured to be repetitively moved forward and backward together with the first mechanical element is disposed on the outer side of the ultrasonic processing portion of the drum, and
the first mechanical element and the second mechanical element are configured to cooperate with each other to subject the web positioned in the ultrasonic processing portion to ultrasonic processing in two steps of moving forward and moving backward but respective home positions of the first and second mechanical elements are drawn apart from each other after completion of the ultrasonic processing in the two steps.

2. The system according to claim 1, wherein the first mechanical element is an ultrasonic horn and the second mechanical element is an anvil.

3. The system according to claim 1, wherein the first mechanical element is the anvil and the second mechanical element is the ultrasonic horn.

4. The system according to claim 2, wherein the anvil is a roll adapted to rotate both in a direction of the forward movement and of the backward movement.

5. The system according to claim 1, further comprising:
biasing means always acting to bias the first mechanical element and the second mechanical element to come close to each other, wherein the biasing means is disposed between the first mechanical element and the second mechanical element.

6. The system according to claim 5, further comprising:
cam means on the outer peripheral surface so as to face the respective home positions to which the first mechanical element and the second mechanical element return after the step of forward movement and the step of backward movement, respectively,
the second mechanical element includes cam follower means associated with the cam means, and
the cam means and the cam follower means are configured to cooperate with each other to draw apart the second mechanical element from the first mechanical element against the biasing effect of the biasing means.

7. The system according to claim 2, wherein
the anvil includes a roll adapted to rotate both in the directions of the forward movement and of the backward movement,
the roll has a peripheral surface facing the horn,
the peripheral surface is formed with a plurality of bosses arranged with certain intervals both in a circumferential direction and in an axial direction so as to form a plurality of rows extending in parallel to each other and diagonally intersecting with the axial direction,
each pair of the adjacent bosses in each of the rows is in such a relationship that, assuming that one boss of adjacent bosses in each of the rows is moved in parallel to the axial direction, the one boss overlaps with a remaining boss, and
each pair of the adjacent rows is in such a relationship that, assuming that one boss disposed at one end portion of one of the adjacent rows is moved in parallel to the axial direction, the one boss at least partially overlaps with at least one boss in a remaining row.

8. A method of subjecting a web continuously running in a machine direction to repetitive ultrasonic processing by a first mechanical element and a second mechanical element facing each other across the web in its thickness direction of the web, said method comprising:
conveying the web continuously in the machine direction while the web is placed on an outer peripheral surface of a drum, said drum being continuously rotated in the machine direction at the same circumferential velocity as a running velocity of the web;
wherein
the first mechanical element is provided on the inside of the drum in an ultrasonic processing portion formed in the outer peripheral surface so as to communicate with both the inside and the outside of the drum and repeats forward movement and backward movement in a direction intersecting the machine direction across the web,
the second mechanical element is provided on the outside of the drum in the ultrasonic processing portion and repeats forward movement and backward movement together with the first mechanical element,
the first mechanical element and the second mechanical element cooperate with each other in two steps of forward movement and backward movement to subject the web positioned at the ultrasonic processing portion to ultrasonic processing but respective home positions of the first and second mechanical elements are drawn apart from each other after completion of the ultrasonic processing in the two steps.

9. The method according to claim 8, wherein the first mechanical element is an ultrasonic horn and the second mechanical element is an anvil.

10. The method according to claim 8, wherein the first mechanical element is the anvil and the second mechanical element is the ultrasonic horn.

11. The method according to claim 8, wherein the anvil is a roll rotating both in directions of the forward movement and of the backward movement.

12. The method according to claim 8, wherein biasing means always acting to bias the first mechanical element and the second mechanical element to come close to each other is disposed between the first mechanical element and the second mechanical element.

13. The method according to claim 12, wherein:
cam means are formed on the outer peripheral surface so as to face the respective home positions to which the first mechanical element and the second mechanical element return after the step of forward movement and the step of backward movement, respectively, and
the second mechanical element is formed with cam follower means associated with the cam means so that these two means cooperate with each other to draw apart the second mechanical element from the first mechanical element against the biasing effect of the biasing means.

14. The method according to claim 9, wherein
the anvil includes a roll rotating both in the directions of the forward movement and of the backward movement,
the roll has a peripheral surface facing the horn,
the peripheral surface is formed with a plurality of bosses arranged with certain intervals both in a circumferential direction and in an axial direction so as to form a plurality of rows extending in parallel to each other and diagonally intersecting with the axial direction,
each pair of the adjacent bosses in each of the rows is in such a relationship that, assuming that one boss of adjacent bosses in each of the rows is moved in parallel to the axial direction, the one boss overlaps with a remaining boss, and
each pair of the adjacent rows is in such a relationship that, assuming that one boss disposed at one end portion of one of the adjacent rows is moved in parallel to the axial direction, the one boss at least partially overlaps with at least one boss in a remaining row.

\* \* \* \* \*